US00PP09628P

United States Patent [19]

Saville

[11] Patent Number: Plant 9,628

[45] Date of Patent: Aug. 20, 1996

[54] MINIATURE ROSE PLANT NAMED 'SAVACRIM'

[75] Inventor: F. Harmon Saville, Rowley, Mass.

[73] Assignee: Nor'East Miniature Roses, Inc., Rowley, Mass.

[21] Appl. No.: 364,593

[22] Filed: Dec. 27, 1994

[51] Int. Cl.[6] ..... A01H 5/00

[52] U.S. Cl. ..... Plt./10

[58] Field of Search ..... Plt./10

[56] References Cited

U.S. PATENT DOCUMENTS

P.P. 5,115 10/1983 Williams ..... Plt./10

P.P. 6,054 12/1987 Laver ..... Plt./10

P.P. 7,061 12/1989 Moore ..... Plt./10

OTHER PUBLICATIONS

Nor'East Miniature Roses, Inc., Supplement 1995, Nor'East Miniature Roses, Inc., Rowley, MA., 3 pages.

*Primary Examiner*—Howard J. Locker

*Attorney, Agent, or Firm*—Christie, Parker & Hale

[57] ABSTRACT

A new miniature rose with crimson flowers and attractive bud and open flower.

1 Drawing Sheet

SUMMARY OF THE INVENTION

The present invention relates to a new and distinct variety of rose plant of the miniature rose class, which was created by me by crossing as seed parent the variety known as 'Savabear' (U.S. Plant Pat. No. 7,424 marketed and sold under the trademark "TEDDY BEAR" and as pollen parent a seedling from 'Zorina' (U.S. Plant Pat. No. 2,321)×'Baby Katie' (U.S. Plant Pat. No. 4,471). The varietal denomination of this new rose is 'Savacrim'.

Among the novel characteristics possessed by this new variety which distinguishes it from its parents and all other varieties of which I am aware is its attractive crimson red flowers and attractive bud and open flower. The new variety differs from its paretns in flower coloration. Whereas the seed parent produces russet-colored flowers and the pollen parent seedling produces red-orange colored flowers, the new variety produces crimson red flowers.

Asexual reproduction by propagation of cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character. Phenotypic expression may vary with light availability, environmental and cultural conditions.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage:

*Seed parent.*—'Savabear'.

*Pollen parent.*—'Zorina'×'Baby Katie'.

Class: Miniature.

The following observations are made of specimens grown under glass in Essex County, Mass., during the month of July.

FLOWER

Blooming habit.—Recurrent.

A. Bud:

(1) *Size.*—Small.

(2) *Form.*—Oval, pointed.

(3) *Color.*—As sepals divide, bud color is near 53A.

(4) *Sepals.*—Longer than bud, lanceolate, slightly bearded with some foliation near 143C flushed with near 183C.

(5) *Peduncle.*—Length — about ⅝ inch. Aspect — straight. Strength — erect. Color — near 149A.

B. Bloom:

(1) *Size.*—Average size when fully expanded — about 1⅛ inches.

(2) *Borne.*—Singly and several together in small sprays.

(3) *Form.*—High centered at first becoming flat, petals remaining loosely rolled under, some outer petals quill to points.

(4) *Petalage.*—Number of petals under normal conditions — about 18–26.

(5) *Color.*—During first two days, inner petals at center of flower near 46A; outer petals near 46A to 46B; base of petals at point of attachment near 7D; reverse of petals near 53B and general tonality from a distance dark red. Random white streaking in petals and petaloids is common. As blooms age, color changes from near 46A to near 45A. The portions of petals exposed to light change color first and eventually the entire petal undergoes color change. The general tonality of the old faded blooms includes bluish hues.

C. Petals:

(1) *Texture.*—Thick, firm.

(2) *Appearance.*—Inside velvety and outside satiny.

(3) *Form.*—Ovate, slight point at apex.
(4) *Arrangement.*—Imbricated, regularly arranged, shingle-like.
(5) *Petaloids in center.*—Up to about 5 petaloids.
(6) *Persistence.*—Drop off cleanly.
(7) *Fragrance.*—None.
(8) *Lasting quality.*—Very long on plant, generally up to 10–12 days, sometimes up to 14 days.

REPRODUCTIVE ORGANS

A. Stamens, filaments and anthers:
*Arrangement and color.*—Regularly arranged around styles. Color — near 9D.
B. Pollen:
*Color.*—Near 13A.
C. Styles: Uneven length.
D. Stigmas:
*Color.*—Near 9C.
E. Hips: None observed.

PLANT

A. Form: Upright.
B. Growth: Vigorous.
*Height attained.*—About 16 to 20 inches; stem length very variable, from about 1 to 3.5 inches.
C. Foliage: Compound 5 to 7 leaflets.
(1) *Size.*—Small.
(2) *Quantity.*—Abundant.
(3) *Color.*—New foliage: Upper side — near between 143A and 137B. Underside — near 137C. Old foliage: Upper side — near 137A. Underside — near 138A.
(4) *Shape.*—Oval, pointed.
(5) *Texture.*—Upper side is semi-glossy; underside is matte.
(6) *Edge.*—Serrated.
(7) *Serration.*—Serrate.
(8) *Leaf stem.*—Color — near 137A. Underside — 147B.
(9) *Stipules.*—Medium, slightly bearded.
(10) *Resistance to disease.*—Blackspot — average. Mildew — average. Rust — average.
D. Wood:
(1) *New wood.*—Color — near 184A. Bark — Smooth.
(2) *Old wood.*—Color — near 144A. Bark — smooth.
E. Thorns:
*Quantity (main stalk).*—Few.
*On laterals from stalk.*—Few.
*Form.*—Long, thin, curved slightly downward.
*Length.*—Short.
*Color.*—Near 184A when young.
*Position.*—Irregular.
*Prickles.*—None.
F. Winter hardiness: Needs protection in severe climates.

I claim:

1. A new and distinct variety of rose plant of the miniature rose class, substantially as shown and described.

* * * * *

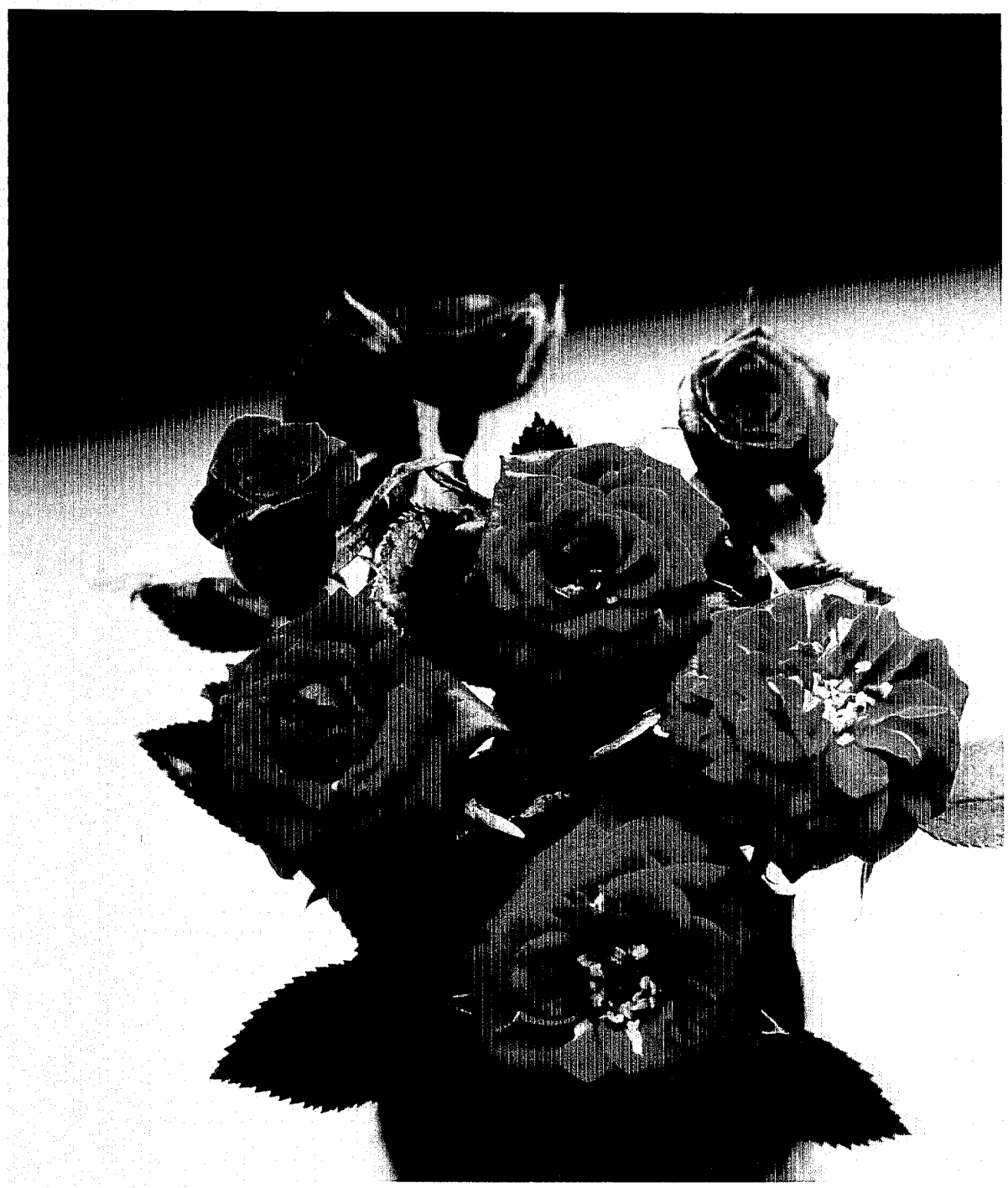

UNITED STATES PATENT AND TRADEMARK OFFICE

CERTIFICATE OF CORRECTION

PATENT NO. : Plant 9,628

DATED : August 20, 1996

INVENTOR(S) : F. Harmon Saville

It is certified that error appears in the above-indentified patent and that said Letters Patent is hereby corrected as shown below:

Column 1, line 15, change "paretns" to -- parents --.

Column 3, line 19, change "9C" to -- 39C --.

Signed and Sealed this

Eighteenth Day of March, 1997

*Attest:*

*Attesting Officer*

BRUCE LEHMAN

*Commissioner of Patents and Trademarks*